United States Patent
Otte

(10) Patent No.: US 7,468,260 B2
(45) Date of Patent: *Dec. 23, 2008

(54) METHOD OF DETECTING AND USING AN EXPRESSION-ENHANCING SEQUENCE

(75) Inventor: Arie Otte, Purmerend (NL)

(73) Assignee: ChromaGenics B.V., Amsterdam (NL)

( * ) Notice: Subject to any disclaimer, the term of this patent is extended or adjusted under 35 U.S.C. 154(b) by 391 days.

This patent is subject to a terminal disclaimer.

(21) Appl. No.: 10/972,684

(22) Filed: Oct. 25, 2004

(65) Prior Publication Data

US 2005/0106609 A1    May 19, 2005

Related U.S. Application Data

(63) Continuation of application No. 09/762,916, filed as application No. PCT/NL99/00518 on Aug. 16, 1999, now Pat. No. 6,872,524.

(30) Foreign Application Priority Data

Aug. 14, 1998 (NL) .................................. 1009862
Nov. 27, 1998 (NL) .................................. 1010670

(51) Int. Cl.
*C12P 21/00* (2006.01)
*C12Q 1/68* (2006.01)
*C12Q 1/02* (2006.01)

(52) U.S. Cl. .............................. 435/70.3; 435/6; 435/29

(58) Field of Classification Search ....................... None
See application file for complete search history.

(56) References Cited

U.S. PATENT DOCUMENTS 5,721,096 A    2/1998    Karathanasis et al.

FOREIGN PATENT DOCUMENTS

| WO | WO 94 29468 | 12/1994 |
| WO | WO 97 10337 | 3/1997 |
| WO | WO 98 11207 | 3/1998 |

OTHER PUBLICATIONS

Mallin et al. Polycomb group repression is blocked by the Drosophila suppressor of Hairy-wing [su(Hw)] insulator. Genetics, vol. 148, pp. 331-339, Jan. 1998.*

Greene et al. Subcloning. Methods in Enzymology, vol. 152, pp. 512-522, 1987.*

* cited by examiner

*Primary Examiner*—Celine Qian
*Assistant Examiner*—Jennifer Dunston
(74) *Attorney, Agent, or Firm*—Amster, Rothstein & Ebenstein LLP

(57) ABSTRACT

The invention relates to a method of detecting a DNA sequence which at least partially contributes to promote the stable expression of a gene. To this end the DNA fragment to be examined is cloned in a vector between i) a DNA sequence involved in the induction of gene transcription repressing chromatin and ii) a reporter gene. The invention also relates to the detected DNA sequence, and the application of a stable expression-enhancing DNA sequence for the stable expression of a gene.

28 Claims, No Drawings

SEQUENCE LISTING

```
<160> NUMBER OF SEQ ID NOS: 5

<210> SEQ ID NO 1
<211> LENGTH: 95
<212> TYPE: DNA
<213> ORGANISM: artificial sequence
<220> FEATURE:
<221> NAME/KEY: misc_feature
<222> LOCATION: (1)..(95)
<223> OTHER INFORMATION: synthetic sequence containing four binding
      sites for LexA from E. coli

<400> SEQUENCE: 1
gtcgactgct gtatataaaa ccagtggtta tatgtacagt acttgtactg tacatataac      60
cactggtttt atacagcaag cttggatccg tcgac                                 95

<210> SEQ ID NO 2
<211> LENGTH: 73
<212> TYPE: DNA
<213> ORGANISM: artificial sequence
<220> FEATURE:
<221> NAME/KEY: primer_bind
<222> LOCATION: (1)..(73)
<223> OTHER INFORMATION: forward primer used to make human heat
      shock factor inducible promoter

<400> SEQUENCE: 2
aagcttggga gtcgaaactt ctggaatatt cccgaacttt cagccgacga cttataaaac      60
gccaggggca agc                                                         73

<210> SEQ ID NO 3
<211> LENGTH: 76
<212> TYPE: DNA
<213> ORGANISM: artificial sequence
<220> FEATURE:
<221> NAME/KEY: primer_bind
<222> LOCATION: (1)..(76)
<223> OTHER INFORMATION: reverse primer used to make human heat shock
      factor inducible promoter

<400> SEQUENCE: 3
ccatggttta gcttccttag ctcctgaaaa tctcgccaag ctcccggggt ccgcgagaag      60
agctcggtcc ttccgg                                                      76

<210> SEQ ID NO 4
<211> LENGTH: 38
<212> TYPE: DNA
<213> ORGANISM: artificial sequence
```

-continued

```
<220> FEATURE:
<221> NAME/KEY: primer_bind
<222> LOCATION: (1)..(38)
<223> OTHER INFORMATION: forward PCR primer used to isolate DNA fragment
      from genomic Drosophila DNA

<400> SEQUENCE: 4
gatcaagctt atgatctgcg tatgatacca aatttctg                              38

<210> SEQ ID NO 5
<211> LENGTH: 36
<212> TYPE: DNA
<213> ORGANISM: artificial sequence
<220> FEATURE:
<221> NAME/KEY: primer_bind
<222> LOCATION: (1)..(36)
<223> OTHER INFORMATION: reverse PCR primer used to isolate DNA fragment
      from genomic Drosophila DNA

<400> SEQUENCE: 5
gacaagctta cattgctggg cgagctgcgc caatcg                                36
```

METHOD OF DETECTING AND USING AN EXPRESSION-ENHANCING SEQUENCE

CROSS-REFERENCE TO RELATED APPLICATIONS

This application is a continuation of U.S. patent application Ser. No. 09/762,916, filed Jun. 29, 2001, now U.S. Pat. No. 6,872,524, which is a national stage entry under 35 U.S.C. §371 of PCT International Patent Application No. PCT/NL99/00518, filed Aug. 16, 1999, and which claims priority of both Dutch Patent Application No. 1009862, filed Aug. 14, 1998, and Dutch Patent Application No. 1010670, filed Nov. 27, 1998, the contents of all of which are hereby incorporated by reference in their entirety.

The present invention relates to a method of detecting, and optionally selecting, a DNA sequence.

It is not easy to detect a specific DNA sequence of which the nucleotide sequence is not known. Despite the fact that genetic manipulation has been employed for decades, predictably bringing to expression a gene in a genetically modified plant, animal or other eukaryotic organism is a problem. Although many microbiological methods of production merely aim at the highest possible expression, in plants or animals the exact level of a gen's expression is for many applications of great importance. Too much expression as well as too little expression may lead to the desired result not being achieved. Also, experience has shown that after sexual reproduction the ability for expression in a subsequent generation is often lost again. It is also difficult to control the moment in time and the location of expression in the organism (tissue specificity).

It is the object of the invention to provide a method of the kind mentioned in the preamble, which makes it possible to select and, if desired, isolate a DNA sequence, whereby the above-mentioned problems can be avoided.

To this end the method according to the preamble is characterized in that the DNA sequence to be detected possesses a stable expression-enhancing quality, which method comprises the steps of 1) the cloning in a vector of DNA fragments having a size of <5000 base pairs between i) a DNA sequence involved in the induction of gene transcription-repressing chromatin, and ii) a reporter gene comprising a promotor, resulting in a variety of a fragment-comprising vectors, wherein the distance between the DNA sequence involved in the induction of the transcription of gene-repressing chromatin and the reporter gene is fewer than 5000 base pairs;
2) introducing the vectors into host cells, in which host cells the promotor may be active but induction of the transcription of gene-repressing chromatin in the vectors results in the repression of the transcription of the reporter gene; and
3) subjecting the host cells to a selection in order to identify a host cell exhibiting reporter gene-activity.

This provides a reliable method of detecting DNA sequences having a stable expression-enhancing quality. If desired, this sequence may be isolated and inserted before another gene. As the DNA in step 1, for example, a restriction enzyme-cleaved DNA from a eukaryotic organism, in particular a plant or a vertebrate, is used wherein the size of the DNA fragments is below 5000 base pairs.

Clearly, when the occasion arises it will be possible to readily distinguish between on the one hand an expression-enhancing sequence ("enhancer"), which in extreme cases would be able to neutralize the transcription-repressing effect of chromatin, and on the other hand the stable expression-enhancing DNA fragment. In the first case the reporter gene in an organism is transformed with a vector comprising the promotor together with the reporter gene but without the transcription-repressing sequence is expressed at a higher level than in an organism transformed with a vector comprising a stable expression-enhancing DNA fragment together with the reporter gene and likewise, without the transcription-repressing sequence.

According to a first preferred embodiment, the selection in step 3) occurs by using a reporter gene which provides resistance to a growth inhibitor and the host cells are cultivated in the presence of the growth inhibitor.

This inhibits the growth of host cells which, without an active resistance gene, are not resistant to the growth inhibitor, and allows the selection of those host cells which possess a stable expression-enhancing DNA sequence.

Preferably, the growth inhibitor is present in a concentration sufficiently high to kill host cells in which the gene providing resistance to the growth inhibitor is not active.

This ensures to a large extent that growing organisms will comprise a vector with the desired DNA sequence.

Very conveniently an antibiotic is used as the growth inhibitor and the reporter gene is a gene providing resistance to the antibiotic.

A great assortment of genes providing resistance to antibiotics is available in the field, making it simple to choose a gene suitable for the host cell. A gene is then chosen which provides resistance to a growth inhibitor to which the host cell is not already resistant of itself.

In accordance with a second embodiment the reporter gene codes for Green Fluorescent Protein.

By means of fluorescence measurement it is then possible to detect and isolate host cells with the desired DNA-comprising vector.

According to a preferred embodiment, fluorescent host cells are separated from non-fluorescent host cells by means of a Fluorescence-Activated Cell Sorter (FACS).

According to a third embodiment the reporter gene is *luciferase*. With the aid of *luciferase* it is possible to perform (semi)-quantitative measurement of the expression.

In step 1) it is preferred that the fragments have a size of substantially between 2000-3000 base pairs.

Fragments of such a size allow a more precise localization of the sequence to be detected without the number of host cells to be screened in step 3) becoming so large that this is going to form an unnecessary work load.

Conveniently, the DNA sequence involved with the transcription induction of gene-repressing chromatin is a DNA sequence that is recognized by a heterochromatin-binding protein comprising HP1 (heterochromatin-binding protein 1), which HP1-comprising complex is expressed in the host cell. According to an alternative method, the DNA sequence is recognized by a complex comprising a Polycomb-group (Pc-G) protein, and the Polycomb-group protein-comprising complex is expressed in the host cell. According to yet another embodiment, the DNA sequence is recognized by a complex possessing a histone deacetylase activity, and the histone deacetylase activity-possessing complex is expressed in the host cell. Finally, according to a further embodiment, the DNA sequence involved in the induction of the transcription of gene-repressing chromatin is a DNA sequence recognized by a protein complex comprising MeCP2 (methyl-CpG-binding protein 2), and the MeCP2-comprising complex is expressed in the host cell.

In this manner four suitable complexes recognizing DNA sequences are provided, while it should be noted that in the event of the complex not being expressed in the host cell, this will not result in false positives and will merely limit the efficiency with which the wanted DNA sequences are detected.

Conveniently, the protein complex comprises a fusion protein, such as a protein complex wherein the first part is a part binding the DNA-binding site of LexA-DNA or GAL4-DNA.

Suitable DNA binding sites of this kind are known in the art and are obtained from bacteria or yeast.

The organism in step 1) is preferably chosen from the group comprising a plant and a vertebrate such as, more particularly, a mammal.

For these organisms applies that, partly due to the large amount of chromosomal DNA, it is practically impossible without the method of the present invention to find the DNA sequence to be detected, since indeed its base sequence is unknown.

According to a further preferred embodiment, the vector is an episomally replicating vector, such as suitably a vector comprising a replication origin from the Epstein-Barr virus (EBV), OriP, and a nuclear antigen (EBNA1).

Such vectors are easy to handle, can be genetically manipulated and are vectors which form a chromatin structure in which the expression is repressed.

The invention further relates to a DNA sequence selected from i) a DNA sequence isolated from a plant or vertebrate, or derivatives thereof, and ii) a synthetic DNA sequence or one constructed by means of genetic engineering, which DNA sequence is a repression-inhibiting sequence which, by the method according to the present invention can be detected, selected and optionally cloned.

More specifically, the invention further relates to a DNA sequence selected from i) a DNA sequence isolated from a plant or vertebrate, or derivatives thereof, and ii) a synthetic DNA sequence or one constructed by means of genetic engineering, which DNA sequence is detected, selected and optionally cloned by the method according to the present invention.

The DNA sequences according to the invention differ from the known DNA sequences in that they are not an enhancer or silencer.

Synthetic DNA sequences may be prepared in accordance with techniques generally known in the art. In particular, it is possible to prepare large numbers of different DNA sequences, and such sequences are commercially available (for example from: Pharmacia Biotech, Uppsala, Sweden). However, such synthetic DNA sequences have to be suitable for cloning in a plasmid. This is generally known in the art and is done, for example, with linkers comprising a restriction cleavage site.

Clearly, the present invention also relates to a method of making a DNA construct comprising a gene that is to be expressed stably, wherein a stable expression-enhancing DNA sequence, selected with the aid of the method according to the invention is inserted at less than 2000 bp from the gene.

This is a more stable and predictable manner of expressing a gene.

Preferably the stable expression-enhancing DNA sequence will be inserted both upstream and downstream from the gene.

It is believed that this further increases the likelihood of a stable gene expression.

Finally, the invention relates to a use of the DNA construct according to the invention, wherein the DNA construct is a vector, for the transformation of an organism which suitably is an organism as defined above.

The present invention will now be further elucidated with reference to the following exemplary embodiments.

EXAMPLE I

To illustrate the principle of the workings of the method according to the invention, scs is used, which is a DNA fragment from *Drosophila* melanogaster which is known to be a boundary element. As can be seen from the example below, scs can be used for blocking the following repressors: HP1, Polycomb-group proteins and MeCP2. In the same manner, DNA fragments from phage lambda have been tested as negative control. Scs (special chromatin structure) was originally isolated as a DNA sequence flanking the heat shock locus (hsp70) in *Drosophila* (Kellum, R. and P. Schedl. 1991. Cell 64: 941-950). They have found that when scs is placed around a reporter gene and is reintroduced in *Drosophila*, the expression of a reporter gene is less variable. They neither reported nor suggested that scs may be used to prevent repression by other repressors, in particular the above-mentioned repressors. Also, Kellum et al. neither reported nor suggested that scs might be used in systems other than *Drosophila* for rendering transgene expression less variable.

For testing the repression-eliminating property of a DNA sequence, two types of vectors are constructed.

The first type of vector comprises in 5'-3' sequence: four LexA binding sites, the scs sequence to be tested, the human heat shock factor-inducible promotor, and the *luciferase* gene as reporter gene. As a control a similar vector is made which instead of the known scs sequence comprises a random fragment (from phage lambda) of a comparable length (both described in point 1 below).

To accomplish repression of the reporter gene in the transformed cell, the second type of vector comprises a gene coding for a fusion protein of LexA and the above-mentioned repressors. A vector of this second type comprises the gene coding for LexA only, or a vector comprises the gene coding for LexA-HP1, etc. (described in point 2 below).

1 A vector coding for EBNA-1 (a nuclear antigen) is the hygromycin resistance gene comprising pREP4 vector (Invitrogen Corporation, Carlsbad, USA). The EBNA-1 sequence is present to ensure that the vector does not (stably) integrate in the genome, but replicates episomally. The promoter (Prsv) of this vector has been removed by digestion with the restriction enzyme SalI and replaced by a synthesized sequence having four binding sites for LexA from *E. coli*. This sequence is from 5'- 3': GTCGACTGCTGTATATAAAACCAGTGGT-TATATGTACAGTACTTGTACTGTA CATATAAC-CACTGGTTTTATATACAGCAAGCTTG-GATCCGTCGAC (SEQ ID NO:1). The 5' side of this sequence comprises a SalI site, the 3' side a HindIII-BamHI-SalI site (all shown in bold type). Downstream from the LexA binding sites in the HindIII and BamHI sites, the human heat shock factor-inducible promoter (0.29 kbp HindIII/NcoI fragment) and the *luciferase* reporter gene inclusive of SV40 polyadenylation signal (1.9 kbp NcoI/BamHI fragment) are cloned in a three-way ligation. The human heat shock factor-inducible promoter (hsp70; accession numbers M59828 and M34267; nucleotides 52 to 244) can be obtained by means of PCR amplification on human genomic DNA (Cat. No. 6550-1; Clontech, Palo Alto, USA). As PCR primers, forward primer 5'- 3': AAGCTTGGGAGTC-GAAACTTCTGGATATTCCCGAACT-TCAGCCGACG ACTTATAAAACGC-CAGGGGCAAGC (SEQ ID NO:2) may be considered;

and as reverse primer 5'- 3': CCATGGTTTAGCTTCCT-TAGCTCCTGAAAATCTCGCCAAGCTCCCGG GGTCCGCGAGAAGAGCTCGGTCCTTCCGG (SEQ ID NO:3) The forward primer comprises a HindIII site, the reverse primer comprises a NcoI site (given in bold print). The luciferase reporter gene inclusive of SV40 polyadenylation signals were obtained through NcoI/BamHI digestion of the pGL3 control vector (Cat. no E1741; Promega, Madison, USA). In the thus obtained vector, in the HindIII site between the LexA binding sites and the heat shock promoter, either a 2.1 kbp HindIII fragment of phage lambda is cloned (Pharmacia Biotech, Uppsala, Sweden), or a 1.7 kbp scs HindIII fragment. The 1.7 kbp scs DNA fragment is isolated from genomic *Drosophila* DNA (Cat. #6940-1, Clontech, Palo Alto, USA) with the aid of PCR primers (Forward primer 5'- 3': GATCAAGC-TTATGATCT-GCGTATGATACCAAATTTCTG (SEQ ID NO:4); Reverse primer 5'- 3': GACAAGCTTACAT-TGCTGGGCGAGCTGCGCCAATCG (SEQ ID NO:5)). At the ends of these primers HindIII restriction enzyme sites were located. The vector with the Lambda fragment (control) is indicated as reporter construct a, the vector with the scs fragment as reporter construct b. Restriction enzyme digestions, PCR amplifications and clonings are performed by standard procedures as described in Sambrook et al., Molecular Cloning; a laboratory manual, second edition.

2 The DNA-binding domain of the LexA protein (aa 1-202) (Cat.#6183-1, Clontech, Palo Alto, USA) is cloned in the HindIII site of the neomycin resistance gene-comprising pREP9 (Invitrogen Corporation, Carlsbad, USA) vector. Downstream and in frame with the LexA gene, one gene coding for a repressor is cloned per vector. The repressors used are: the 1674 bp-long coding part of the humane Polycomb-group gene HPC2 (accession number GENBANK®: AAB80718), the 1131 bp-long coding part of the humane Polycomb-group gene RING1(accession number GENBANK®: Z14000), the 4098 bp-long coding part of the *Drosophila* Polycomb-group gene Su(z)2 (accession number GENBANK®: CAA41965), the 558 bp coding part of M32 (mHP1) (accession number GENBANK®: P23197), or the 1478 bp coding part of MeCP2 (accession number GENBANK®: A41907). These constructs code for LexA-HPC2, LexA-RING1, LexA-Su(z)2, LexA-mHP1 and LexA-MeCP2 fusion proteins, or LexA repressors. These bind to the LeXA binding sites (see point 1).

3 The reporter vectors a and b and the LexA repressor-coding vectors are expressed in humane U-2 OS (osteosarcoma) cells obtained from the ATTC (accession number HTB-96). Transfection of the cells with the DNA constructs is performed using the calcium phosphate method in accordance with the instructions of the manufacturer of the transfection kit (Cat. No. 18306-019, Gibco BRL, Gaithersburg, USA). The osteosarcoma cells grow in the presence of 100 µg/ml neomycin (G418: Cat. No. 1464981; Boehringer/Roche, Switzerland) and 50 µg/ml hygromicin B (Cat. No 843555; Boehringer/Roche, Switzerland). Three days after transfection a heat shock is given (43° C. for 1 hour, followed by a 6-hour recovery period at 37° C.). This treatment activates the *luciferase* gene and causes the production of the *luciferase* reporter protein. The enzymatic activity of this *luciferase* protein is a measure of the transcription induction that has been induced. Cells are purified and the *luciferase* enzyme activity is measured, all in compliance with the manufacturer's instructions for the standard *luciferase* reporter gene assay kit (Cat. No. 1814036; Boehringer/Roche, Switzerland).

Result

4 In cells in which the reporter construct a (with the Lambda fragment) is expressed, but no LexA repressors, the *luciferase* gene is expressed after heat shock. This is the 100% value.

5 In cells in which the reporter construct b (with the scs fragment) is expressed, but no LexA repressors, the *luciferase* gene is expressed after heat shock up to a value of 100%. Since this value does not exceed the 100% it shows, as explained earlier, that it is not an expression-increasing sequence.

6 In cells in which the reporter construct a (with the Lambda fragment) is expressed, and also LexA repressors are expressed, the expression of the *luciferase* gene after heat shock is repressed to an average of 20%.

7 In cells in which the reporter construct b (with scs fragment) is expressed, and at the same time LexA repressors, the expression of the *luciferase* gene after heat shock reaches a value of 100%. This shows that the induction of the repressor activity can be repressed with scs.

EXAMPLE II

Instead of *luciferase* as reporter gene, it is according to the present invention also possible to use another reporter gene. It is also possible to use other promoters.

8 In the reporter constructs a and b the *luciferase* reporter gene has been replaced by the Zeocin resistance gene. The heat shock promoter has been replaced by the constitutive SV40 promotor (pSV40/ZEO; Cat. No. V502-20; Invitrogen, Carlsbad, USA). After transfection the U-2 OS cells grow in 250 µg/ml Zeocin (Cat. No. R250-01: Invitrogen, Carlsbad, USA) and 100 µg/ml neomycin (G418: Cat. No. 1464981; Boehringer/Roche, Switzerland).

9 Cells that have been transfected with the selection construct comprising a 2.1 kbp Lambda fragment and also with a construct that expresses a LexA repressor, die after 20-30 days. This shows that the Lambda fragment is not able to overcome the repression of the gene with which antibiotics resistance is achieved.

10 Cells that are transfected with the selection construct comprising the scs fragment and also with a construct that expresses a LexA repressor, do not die but continue to grow. This also shows that with the boundary element scs the repression can be overcome and that the method according to the present invention can be employed using a variety of promotors and reporter genes.

EXAMPLE III

The sequences found and selected by the method according to the invention can be used to combat repression in an organism other than that from which the sequence is derived.

11 Two new constructs, c and d, are made, so-called T-DNA constructs, which are suitable for the transformation of plants.

12 Construct c comprises a cassette with the NPTII (neomycin phosphotransferase II) gene for resistance selection with kanamycin and the GUS (β-glucuronidase) reporter gene. The NPTII gene is regulated by the constitutive nos promotor and the GUS reporter gene by the constitutive CaMV 35S promotor (Mlynarova, L. et al., 1995. The Plant Cell 7: 599-609).
13 Construct d is construct c in which an scs fragment is cloned immediately upstream from the GUS-CaMV/nos-NPTII cassette and an scs fragment immediately downstream from the cassette.
14 *Agrobacterium tumefaciens* is transformed with construct c or d. *Arabidopsis* plants are submerged in a suspension (culture) of *Agrobacterium tumefaciens* with construct c and in a suspension of *Agrobacterium tumefaciens* with construct d (Clough et al., 1998. The Plant J. 16: 735-743).
15 40 individual *Arabidopsis* plants with construct c or d are raised and the seeds of the plants collected. The seeds are sown onto a medium containing kanamycin (Cat. No. 106801; Boehringer/Roche, Swiss) and GUS reporter activity is measured in the leaves of the developed plants.
16 The GUS activity in plants with construct c is very variable (7 high; 6 intermediate; 11 low; 16 zero); the GUS activity in plants with construct d is systematically higher and the variability is reduced (26 high; 4 intermediate; 5 low; 5 zero).
17 This shows that a gene can be expressed more stably with a boundary element, even if this boundary element does not originate from the same organism.

The invention claimed is:

1. A method of analyzing and/or isolating a DNA sequence having a stable expression-enhancing quality, the method comprising the steps of:
   a) cloning DNA fragments into vectors at a location between
      i) a DNA sequence comprising a binding site for a repressor protein, which binding site comprises a LexA-binding site or a GAL4-binding site, and wherein the repressor protein is involved in the induction of gene-transcription repressing chromatin, and wherein the repressor protein comprises a fusion protein comprising a part binding a LexA-binding site or a part binding a GAL4-binding site, and
      ii) a reporter gene comprising a promoter, resulting in a variety of fragment-comprising vectors;
   b) introducing the vectors into host cells;
   c) subjecting the host cells to a selection step in order to identify host cells comprising vectors comprising a DNA sequence having a stable expression-enhancing quality, wherein the repressor protein is present in the host cells; and
   d) isolating from the vectors the DNA sequence having a stable expression-enhancing quality.

2. A method for making an expression construct for stable expression of a gene of interest, said method comprising:
   providing a DNA sequence having transcription-enhancing quality obtained by a method according to claim 1, and
   cloning said DNA sequence into an expression construct comprising a gene of interest that is to be expressed.

3. The method of claim 2, wherein the DNA sequence having transcription-enhancing quality is cloned at less than 2000 bp from the gene of interest.

4. The method of claim 2, wherein the DNA sequence having transcription-enhancing quality is cloned both upstream and downstream from the gene of interest.

5. A method for obtaining a host cell comprising an expression construct for stable expression of a gene of interest, said method comprising:

providing an expression construct for stable expression of a gene of interest obtained by a method according to claim 2, and
introducing said expression construct into a host cell.

6. A method for stably expressing a gene of interest in a host cell, said method comprising:
   culturing a host cell obtained by a method according to claim 5, and expressing the gene of interest from the expression construct in the host cell.

7. The method of claim 1, wherein the promoter may be active in the host cells but wherein induction of gene-transcription repressing chromatin in the vectors results in the repression of transcription of the reporter gene.

8. The method of claim 1, wherein the selection in step c) occurs by using a reporter gene which provides resistance to a growth inhibitor, and the host cells are cultivated in the presence of the growth inhibitor.

9. The method of claim 8, wherein the growth inhibitor is present in a concentration sufficiently high to kill host cells in which the gene providing resistance to the growth inhibitor is not active.

10. The method of claim 9, wherein an antibiotic is used as the growth inhibitor and the reporter gene provides resistance to the antibiotic.

11. The method of claim 10, wherein the antibiotic is zeocin.

12. The method of claim 1, wherein the reporter gene codes for luciferase.

13. The method of claim 1, wherein the reporter gene codes for a Green Fluorescent Protein.

14. The method of claim 13, wherein the host cells are selected using a Fluorescence-Activated Cell Sorter.

15. The method of claim 1, wherein the cloned DNA fragments have a size of fewer than 5,000 base pairs.

16. The method of claim 1, wherein the fusion protein comprises a part binding a LexA-binding site.

17. The method of claim 1, wherein the fusion protein comprises a part binding a GAL4-binding site.

18. The method of claim 1, wherein the DNA fragments in step a) are isolated from the genome of a plant or a vertebrate.

19. The method of claim 18, wherein the vertebrate is a mammal.

20. The method of claim 1, wherein the vector is an episomally replicating vector.

21. The method of claim 20, wherein the vector comprises a replication origin from the Epstein-Barr virus (EBV), OriP, and EBV nuclear antigen-1(EBNA1).

22. The method according to claim 1, wherein the host cells are human U-2 OS cells.

23. The method according to claim 1, wherein the promoter is a SV40 promoter.

24. The method of claim 1, wherein the repression-inducing protein comprises heterochromatin-binding protein 1 (HP1).

25. The method according to claim 1, wherein the repression-inducing protein comprises a Polycomb-group (PcG) protein.

26. The method according to claim 25, wherein the PcG protein is selected from the group consisting of HPC2, RING1, and Su(z)2.

27. The method according to claim 1, wherein the repression-inducing protein comprises a protein having histone deacetylase activity.

28. The method according to claim 1, wherein the repression-inducing protein comprises methyl-CpG-binding protein 2 (MeCP2).

* * * * *